(12) United States Patent
Traber et al.

(10) Patent No.: US 8,658,787 B2
(45) Date of Patent: Feb. 25, 2014

(54) GALACTO-RHAMNOGALACTURONATE COMPOSITIONS FOR THE TREATMENT OF NON-ALCOHOLIC STEATOHEPATITIS AND NON-ALCOHOLIC FATTY LIVER DISEASE

(75) Inventors: Peter G. Traber, Duluth, GA (US); Eliezer Zomer, Newton, MA (US); Anatole A. Klyosov, Newton, MA (US)

(73) Assignee: Galectin Therapeutics Inc., Norcross, GA (US)

( * ) Notice: Subject to any disclaimer, the term of this patent is extended or adjusted under 35 U.S.C. 154(b) by 0 days.

(21) Appl. No.: 13/573,454

(22) Filed: Sep. 14, 2012

(65) Prior Publication Data

US 2013/0171151 A1   Jul. 4, 2013

Related U.S. Application Data

(60) Provisional application No. 61/535,655, filed on Sep. 16, 2011, provisional application No. 61/656,288, filed on Jun. 6, 2012.

(51) Int. Cl.
*C08B 37/06* (2006.01)
*C08B 37/00* (2006.01)
*A61K 31/732* (2006.01)

(52) U.S. Cl.
CPC ........... *C08B 37/0045* (2013.01); *C08B 37/006* (2013.01); *A61K 31/732* (2013.01)
USPC .......................................... 536/123; 536/114

(58) Field of Classification Search
None
See application file for complete search history.

(56) References Cited

U.S. PATENT DOCUMENTS

| 5,434,141 | A | 7/1995 | Schafer et al. |
| 8,128,966 | B2 * | 3/2012 | Staples et al. ................. 424/725 |
| 2001/0039048 | A1 | 11/2001 | Wu et al. |
| 2002/0155513 | A1 | 10/2002 | Hsu et al. |
| 2003/0186933 | A1 | 10/2003 | Yoo |
| 2004/0241138 | A1 | 12/2004 | Hsu |
| 2008/0089959 | A1 | 4/2008 | Chang et al. |
| 2008/0107622 | A1 * | 5/2008 | Platt et al. .................... 424/85.2 |
| 2009/0028925 | A1 | 1/2009 | Erion et al. |
| 2009/0221533 | A1 | 9/2009 | Puder et al. |
| 2011/0008903 | A1 | 1/2011 | Paradis et al. |
| 2011/0082119 | A1 | 4/2011 | Yano |
| 2012/0282220 | A1 * | 11/2012 | Platt et al. .................... 424/85.2 |

OTHER PUBLICATIONS

Castaño et al., "Serum Amyloid P Inhibits Fibrosis Through FcγR-Dependent Monocyte-Macrophage Regulation in Vivo" Sit Transl Med (2009) vol. 1 No. 5 pp. 1-26.*
Duvnjak et al., "Therapy of Nonalcoholic Fatty Liver Disease: Current Status" Journal of Physiology and Pharmacology (2009) vol. 60 Suppl. 7 pp. 57-66.*
U.S. Appl. No. 13/726,900, filed Dec. 2012, Platt et al.*
International Search Report and Written Opinion issued in connection with International Appln. No. PCT/US2012/055360 on Nov. 20, 2012.
Castano et al., "Serum Amyloid P Inhibits Fibrosis Through FcγR-Dependent Monocyte-Macrophage Regulation in Vivo", Sci Transl Med., Nov. 4, 2009, pp. 1-26.

* cited by examiner

*Primary Examiner* — Eric S Olson
(74) *Attorney, Agent, or Firm* — Greenberg Traurig, LLP

(57) ABSTRACT

Aspects of the invention provide methods for treatment of nonalcoholic steatohepatitis and associated liver fibrosis. In particular, aspects of the invention relate to the use of a therapeutic formulation comprising a galacto-rhamnogalacturonate compound for the treatment of nonalcoholic steatohepatitis and associated liver fibrosis.

44 Claims, 9 Drawing Sheets
(8 of 9 Drawing Sheet(s) Filed in Color)

A.

B.

A.

B.

GALACTO-RHAMNOGALACTURONATE COMPOSITIONS FOR THE TREATMENT OF NON-ALCOHOLIC STEATOHEPATITIS AND NON-ALCOHOLIC FATTY LIVER DISEASE

CROSS-REFERENCE TO RELATED APPLICATIONS

This application claims the benefit of and priority to U.S. provisional Application Ser. No. 61/535,655, filed Sep. 16, 2011, and U.S. provisional Application Ser. No. 61/656,288, filed Jun. 6, 2012, the entire disclosure of each of which is incorporated herein by reference in their entireties.

BACKGROUND OF THE INVENTION

Nonalcoholic fatty liver disease (NAFLD) and steatohepatitis (NASH) are common liver disorders in the United States. Histopathologically, these disorders resemble alcoholic liver disease, but they occur in people who drink little or no alcohol. The pathological changes in the liver include, but are not limited to, fat accumulation in hepatocytes, evidence of hepatocellular degeneration, infiltrates of inflammatory cells, deposition of excess fibrous tissue, hepatocellular nodule formation, cirrhosis, and hepatocellular carcinoma. To date, no specific therapies for these disorders exist. Therefore, there is a need to provide methods for treatment of nonalcoholic steatohepatitis with or without associated liver fibrosis.

SUMMARY OF THE INVENTION

Aspects of the invention relate to methods of treating a subject having a fatty liver, nonalcoholic fatty liver disease (NALFD), nonalcoholic steatohepatitis (NASH), nonalcoholic steatohepatitis with liver fibrosis, nonalcoholic steatohepatitis with cirrhosis, or nonalcoholic steatohepatitis with cirrhosis and hepatocellular carcinoma, using a therapeutic composition comprising a galactose-containing polysaccharide compound in an acceptable pharmaceutical carrier for parenteral or enteral administration. In some aspects, the invention relate to compositions having a galacto-rhamnogalacturonate compound for the treatment of fatty liver, NALFD, NASH, NASH with liver fibrosis, NASH with cirrhosis, or NASH with cirrhosis and hepatocellular carcinoma. Other aspects of the invention relate to the use of a galacto-rhamnogalacturonate compound in the manufacture of a pharmaceutical composition for the treatment of fatty liver, NALFD, NASH, NASH with liver fibrosis, NASH with cirrhosis, or NASH with cirrhosis and hepatocellular carcinoma. In some embodiments, an admixture having a galacto-rhamnogalacturonate and a therapeutic agent can be used for the treatment or in the manufacture of a pharmaceutical composition for treatment of fatty liver, NALFD, NASH, NASH with liver fibrosis, NASH with cirrhosis, or NASH with cirrhosis and hepatocellular carcinoma.

In some embodiments, the galactose-containing polysaccharide compound is a galacto-rhamnogalacturonate or a galactoarabino-rhamnogalacturonate.

In some embodiments, the method comprises the steps of obtaining a composition for parenteral or enteral administration comprising a galacto-rhamnogalacturonate compound in an acceptable pharmaceutical carrier; administering to a subject an effective dose of the composition for parenteral administration, the subject having one of a fatty liver, NALFD, NASH, NASH with liver fibrosis, NASH with cirrhosis, or NASH with cirrhosis and hepatocellular carcinoma.

In some embodiments, the effective dose of the composition, when administered in a subject in need thereof, can result in reduction of at least one point in severity of NALFD or NASH grading scoring systems, reduction of the level of serum markers of NASH activity, reduction of NASH disease activity or reduction in the medical consequences of NASH.

In some embodiments, the effective dose of the composition, when administered in a subject in need thereof, can result in the reduction in the accumulation of fat in the liver (steatosis) as determined from liver histological sections by assessment of micro-vesicular and macro-vesicular fat particles in hepatocytes or by non-invasive imaging methods including but not limited to ultrasound or magnetic resonance. In some embodiments, the accumulation of fat in the liver is reduced by at least 10% as assessed in percentage of hepatocytes with fat and graded as per NAFLD grading system or by image analysis.

In some embodiments, the effective dose of the composition, when administered in a subject in need thereof, can result in the reduction of hepatocyte ballooning as determined from liver histological section by assessment of swelling of hepatocytes indicating toxicity and inability to regulate cellular volume. In some embodiments, the hepatocyte ballooning is reduced by at least 10% as assessed in percentage of swollen hepatocytes and graded as per NAFLD grading system.

In some embodiments, the effective dose of the composition, when administered in a subject in need thereof, can result in the reduction in the infiltration of inflammatory cells in liver histological specimens, as assessed by the number of neutrophils and lymphocytes in portal, central and lobular areas of the liver specimens. In some embodiments, the infiltration of inflammatory cells in liver histological specimens is reduced by at least 10% less as assessed in percentage of inflammatory cells graded using the NAFLD grading system.

In some embodiments, the effective dose of the composition, when administered in a subject in need thereof, can result in the reduction of accumulation of collagen in the liver as determined by quantitative analysis of Sirius Red staining of liver histological sections. In some embodiments, the reduction of accumulation of collagen in the liver is reduced by at least 5% less as assessed in percentage of liver tissue staining positive for Sirius red indicating collagen.

In some embodiments, the effective dose of the composition, when administered in a subject in need thereof, can result in the reduction in the level of the serum markers of NASH activity. In some embodiments, the serum markers of NASH activity can include, but are not limited to, serum levels of transaminases, serum levels of coenzyme Q reduced or oxidized, or a combination of other serum markers of NASH activity known in the art.

In some embodiments, the effective dose of the composition, when administered in a subject in need thereof, can result in the reduction of liver fibrosis or cirrhosis based on evidence comprising a reduction of the level of the biochemical markers of fibrosis, non invasive testing of liver fibrosis or cirrhosis or liver histologic grading of fibrosis or cirrhosis.

In some embodiments, the effective dose of the composition, when administered in a subject in need thereof, can result in the reduction of at least one point in severity of NAFLD or NASH grading scoring systems including but not limited to NAFLD activity score (NAS), proposed by the NASH Clinical Research Network (established in 2002 by the National Institute of Diabetes and Digestive and Kidney Diseases (NIDDK)), a widely used scoring system.

In some embodiments, the effective dose of the composition, when administered in a subject in need thereof, can result in the reduction in the medical consequences of NASH with liver fibrosis or cirrhosis such as portal hypertension, reduced hepatic protein synthesis, hyperbilirubinemia, or encephalopathy.

In some embodiments, the compound is a polysaccharide and may be chemically defined as galacto-rhamnogalacturonate (GA-RG). In some embodiments, the galacto-rhamnogalacturonate is a selectively depolymerized, branched heteropolymer having a backbone predominantly comprising 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal). In some embodiments, the compound is a galactoarabino-rhamnogalacturonate having a backbone predominantly comprising 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal) and 1,5-α-L-arabinose (Ara) residues. Other side chain minor constituents may include xylose (Xyl), glucose (Glu), and fucose (Fuc).

In some embodiments, the galactoarabino-rhamnogalacturonate comprises 1,4-β-D-galactose and 1,5-α-L-arabinose residues present in a 2:1 or a 3:1 ratio. In some embodiments, the galactoarabino-rhamnogalacturonate comprises 1,4-β-D-galactose residues, 1,5-α-L-arabinose residues or a combination thereof which represent at least 10 molar percent of the total molar carbohydrates.

In some embodiments, the galacto-rhamnogalacturonate or galactoarabino-rhamnogalacturonate has an average molecular weight ranging from 5 kDa to 55 kDa, 2 kDa to 80 kDa or 20 kDa to 70 kDa.

In some embodiments, the compound is a galacto-rhamnogalacturonate and can be used in combination with a therapeutically effective amount of a therapeutic agent. In some embodiment, the galacto-rhamnogalacturonate can be used in admixture.

In some embodiments, the compound is a galacto-rhamnogalacturonate used in combination with a therapeutically effective amount of cysteamine or a pharmaceutically acceptable salt thereof, or cystamine or a pharmaceutically acceptable salt thereof.

In another embodiment, the compound is a galacto-rhamnogalacturonate used in combination with a therapeutically effective amount of various anti-oxidant compounds including but not limited to parenteral or oral administration of compositions comprising glycyrrhizin, schisandra, ascorbic acid, L-glutathione, silymarin, lipoic acid, and d-alpha-tocopherol.

In another embodiment, the compound is a galacto-rhamnogalacturonate used in combination with a therapeutically effective amount of various anti-oxidant compounds including but not limited to parenteral or oral administration of compositions comprising a water soluble Vitamin E preparation, mixed carotenoids, or selenium.

In another embodiment, the compound is a galacto-rhamnogalacturonate used in combination with a therapeutically effective amount of parenteral or oral administration of lecithin or vitamin B complex.

In another embodiment, the compound is a galacto-rhamnogalacturonate used in combination with a therapeutically effective amount of bile salt preparations including but not limited to ursodeoxycholic acid, chenodeoxycholic acid of other naturally occurring or synthetic bile acids or bile acid salts.

In another embodiment, the compound is a galacto-rhamnogalacturonate used in combination with a therapeutically effective amount of antagonists and/or inverse agonists of the Cannabinoid-1 (CB1) receptor.

In another embodiment, the compound is a galacto-rhamnogalacturonate used in combination with a therapeutically effective amount of a PPAR (peroxisome proliferator-activated receptor) activity regulators.

In another embodiment the compound is a galacto-rhamnogalacturonate used in combination with a therapeutically effective amount of a benzothiazepine or benzothiepine compound represented by the following formula having a thioamide bond and a quaternary ammonium substituent.

In another embodiment the compound is a galacto-rhamnogalacturonate used in combination with a therapeutically effective amount of an RNA antisense construct to inhibit protein tyrosine phosphatase PTPRU.

In another embodiment the compound is a galacto-rhamnogalacturonate used in combination with a therapeutically effective amount of a heteroatom-linked substituted piperidine and derivatives thereof useful as histamine H.sub.3 antagonists.

In another embodiment the compound is a galacto-rhamnogalacturonate used in combination with a therapeutically effective amount of a axacyclopentane derivative that inhibits stearoyl-coenzyme alpha delta-9 desaturase.

In another embodiment the compound is a galacto-rhamnogalacturonate used in combination with a therapeutically effective amount of a acylamide compound having secretagogue or inducer activity of adiponectin.

In another embodiment the compound is a galacto-rhamnogalacturonate used in combination with a therapeutically effective amount of quaternary ammonium compounds.

In another embodiment the compound is a galacto-rhamnogalacturonate used in combination with a therapeutically effective amount of a isoflavone compound.

In another embodiment the compound is a galacto-rhamnogalacturonate used in combination with a therapeutically effective amount of a macrolide antibiotic.

In another embodiment the compound is a galacto-rhamnogalacturonate used in combination with a therapeutically effective amount of Glatiramer acetate (also known as Copolymer 1, Cop-1, or Copaxone—as marketed by Teva Pharmaceuticals), an immunomodulator drug currently used to treat multiple sclerosis.

In another embodiment, the compound is a galacto-rhamnogalacturonate used in combination with a therapeutically effective amount of pentraxin proteins, including but not limited to recombinant pentraxin-2.

In another embodiment the compound is galacto-rhamnogalacturonate used in combination with a therapeutically effective amount of a stain, for example but not limited to HMG-CoA reductase inhibitors such as atorvastatin and simvastatin.

In another embodiment the compound is a galacto-rhamnogalacturonate used in combination with a therapeutically effective amount of an n-acetyl cysteine, In another embodiment the compound is a galacto-rhamnogalacturonate used in combination with a therapeutically effective amount of another galectin inhibitor that may inhibit single galectin proteins or a set of galectin proteins including but not limited small organic inhibitors of galectin, monoclonal antibodies, RNA inhibitors, small binding peptides, or protein inhibitors.

In another embodiment the compound is a galacto-rhamnogalacturonate used in combination with a therapeutically effective amount of a monoclonal antibody to inhibit lysyl oxidase (or other like enzymes that crosslink collagen), or a monoclonal antibody to connective tissue growth factor.

In some embodiments, the efficacy of the composition for parenteral administration can be determined by administering the composition to animal models of NASH, including but not limited to, mice rendered diabetic and fed a high fat diet. In some embodiments, administration of the composition to animal models of NASH can result in at least 5% reduction in hepatocellular fat accumulation, at least 5% reduction in liver infiltration of inflammatory cells, or at least a 5% reduction in liver collagen content as determined by morphometric quantification.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be further explained with reference to the attached drawings, wherein like structures are referred to by like numerals throughout the several views. The drawings shown are not necessarily to scale, with emphasis instead generally being placed upon illustrating the principles of the present invention.

DETAILED DESCRIPTION OF THE INVENTION

Figure 1:
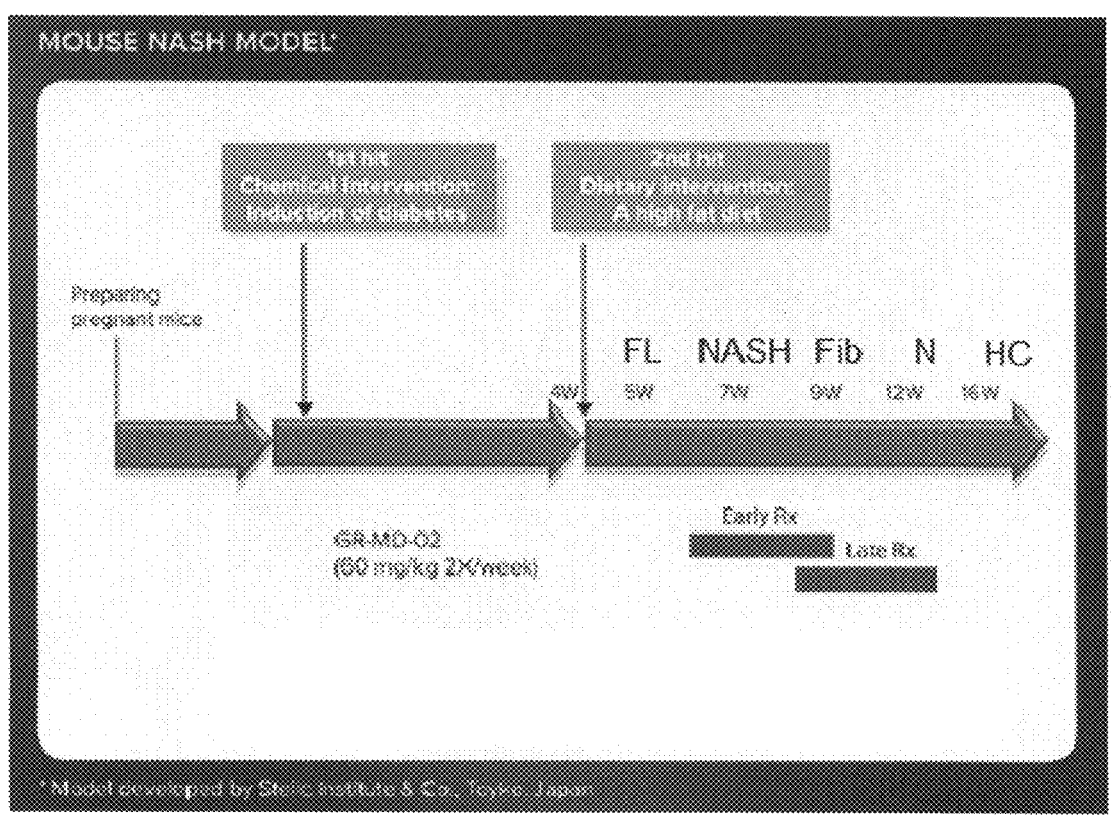
FIG. 1 shows the Experimental Design of Therapy in STAM Mouse Model of Steatohepatitis

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention. Unless otherwise specified, all percentages expressed herein are weight/weight.

The major feature in Nonalcoholic Fatty Liver Disease (NAFLD) is fat accumulation in hepatocytes with minimal inflammation. These patients are usually identified on the basis of a liver biopsy performed because of mildly elevated liver transaminase levels in the serum or the suspicion of fatty liver on non-invasive testing such as computerized tomography or ultrasound.

A subset of individuals with NAFLD are found to have Nonalcoholic Steatohepatitis (NASH) which is fatty liver with the addition of the development of infiltration of inflammatory cells (including but not limited to neutrophils or lymphocytes) within the lobule, central vein and portal areas and evidence of damage to hepatocytes including but not limited to ballooning degeneration. This inflammatory state of NASH may result in the deposition of fibrous tissue, including but not limited to collagen, which can lead to cirrhosis, nodule formation, and eventually hepatocellular carcinoma.

The disease progress is insidious since most people with NASH feel well and are not aware that they have a liver problem. Despite the lack of symptoms, NASH can be severe and can lead to the deposition of fibrotic material in the liver which can result in severe scarring and/or cirrhosis and, in some cases, hepatocellular carcinoma. Therefore, there is a need for clinical tests that could identify NASH early and follow its progression.

NAFLD and NASH are common disorders. It is reported by the U.S. National Institutes of Health that 10-20 percent of Americans have NAFLD and 3-5 percent have NASH. Both disorders are becoming more common because of the greater numbers of people with obesity and diabetes, including children and adolescents. The fact that NASH can progress to cirrhosis makes this a major health problem.

Although NASH has become more common, its underlying cause is still not clear. It most often occurs in middle-aged persons who overweight or obese, many of whom have metabolic syndrome, insulin resistance, or overt diabetes. However, NASH is not simply obesity that affects the liver. NASH can affect children and adolescents.

The proximal cause of liver injury in NASH is not known. Multiple theories have been proposed. Some of these theories include hepatocyte resistance to the action of insulin, production of inflammatory cytokines by fat cells and other inflammatory cells that damage the liver and recruit additional inflammatory cells and oxidative stress in hepatocytes with production of reactive oxygen radicals that damage liver cells and induce inflammation.

Currently, no specific therapies for NASH exist and only general health recommendations are currently provided to patients. These include weight reduction, eating a balanced and healthy diet, increasing physical activity, and avoidance of alcohol and unnecessary medications. Weight loss can improve serum liver tests in some patients with NASH and may improve evidence of histological liver damage, but it does not reverse severe liver disease. In addition, not all patients with NASH are overweight.

A variety of experimental approaches have been evaluated, or are under evaluation in patients with NASH including to the use of antioxidants, such as vitamin E, selenium, betaine, and anti-diabetic agents including metformin, rosiglitazone, and pioglitazone. All clinical results to date have been disappointing.

The galectin-3 protein has recently been implicated in the pathogenesis of NASH. Galectins (also known as galaptins or S-lectin) are a family of lectins which bind beta-galactoside. Galectin as general name was proposed in 1994 for a family of animal lectins (Barondes, S. H., et al.: Galectins: a family of animal b-galactoside-binding lectins. Cell 76, 597-598, 1994), The family is defined by having at least one characteristic carbohydrate recognition domain (CRD) with an affinity for beta-galactosides and sharing certain sequence elements. Within the same peptide chain, some galectins have a CRD with only a few additional amino acids, whereas others have two CRDs joined by a link peptide, and one (galectin-3) has one CRD joined to a different type of domain. The galectin carbohydrate recognition domain (CRD) is a beta-sandwich of about 135 amino acids. The two sheets are slightly bent with 6 strands forming the concave side and 5 strands forming the convex side. The concave side forms a groove in which carbohydrate is bound (Leffler H, Carlsson S, Hedlund M, Qian Y, Poirier F (2004). "Introduction to galectins". Glycoconj. J. 19 (7-9): 433-40).

A wide variety of biological phenomena have been shown to be related to galectins, e.g., development, differentiation, morphogenesis, tumor metastasis, apoptosis, RNA splicing, etc. However, relatively little is known about the mechanism by which galectins exert these functions, particularly in terms of carbohydrate recognition.

Generally, the carbohydrate domain binds to galactose residues associated with glycoproteins. At least fifteen mammalian galectin proteins have been identified which have one or two carbohydrate domain in tandem.

Each galectin protein has a galactose binding domain and other domains that allow homo- or hetero-dimerization to other galectin proteins. Galectin proteins are expressed in a broad range of cells and tissues at low levels under physiological conditions and are found in the nucleus, cytoplasm, and are secreted into the extracellular space by a non-traditional secretory pathway.

The galactose binding domain of galectins binds to galactose containing glycoproteins located on the cell surface or on extracellular matrix proteins. The dimerization domains on galectins promote interaction of galectin proteins, thereby creating interaction between membrane or matrix glycoproteins. These interactions promote cell-cell, cell-matrix, and matrix-matrix interactions and association of membrane receptors that can cause activation, inactivation, or modulation of cell receptor activity leading to modulation of intracellular signaling and subsequent events.

Certain galectin proteins are markedly up-regulated and secreted in high amounts from cells in pathological situations. Multiple inflammatory cells, including but not limited to macrophages and lymphocytes, in tissue inflammation states and repair (fibrosis, scarring) express galectins, particularly galectin-1 and galectin-3.

Mice that lack the galectin-3 gene have been used to explore the function of galectin-3 in a number of disease states that include inflammation and fibrogenesis as key components. These galectin-3 knockout mice have been shown to be resistant to liver fibrogenesis due to toxin administration, lung fibrogenesis, and kidney fibrogenesis.

Galectin-3 knockout mice have also been used to explore the importance of galectin-3 in NASH. In these experiments, mice were fed a high fat diet to induce the development of NAFLD and NASH. Normal mice readily developed fatty liver, inflammatory infiltrates in the liver and liver fibrosis. In stark contrast, the galectin-3 knockout mice did not develop as much fatty liver, and had minimal inflammatory infiltrate and fibrosis. These data suggest that galectin-3 might be an important target for therapy of NASH.

Inhibition of galectin-3 is one potential mechanism underlying the efficacy of galacto-rhamnogalacturonate in this invention.

The term "effective dose" means the amount of galacto-rhamnogalacturonate or other agent in combination with galacto-rhamnogalacturonate that, when administered as a parental dose or in an oral formulation to an animal or human with NAFLD, NASH, or NASH with fibrosis or cirrhosis, is capable of improving NAS score by at least one point or reducing percent collagen area by at least 5%.

In some aspects, methods for treating (e.g., controlling, relieving, ameliorating, alleviating, or slowing the progression of) or methods for preventing (e.g., delaying the onset of or reducing the risk of developing) one or more diseases, disorders, or conditions in which galectins are involved, in a subject in need thereof are featured. The methods include administering to the subject an effective amount of a galacto-rhamnogalacturonate compound, or a composition comprising the galacto-rhamnogalacturonate compound, to a subject having one of a fatty liver, NALFD, NASH, NASH with liver fibrosis, NASH with cirrhosis, or NASH with cirrhosis and hepatocellular carcinoma.

The term "pharmaceutically acceptable carrier" refers to any and all solvents, dispersion media, e.g., human albumin or cross-linked gelatin polypeptides, coatings, antibacterial and antifungal compounds, isotonic, e.g., sodium chloride or sodium glutamate, and absorption delaying compounds, and the like that are physiologically compatible. The use of such media and compounds for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

The term "efficacy" refers in some embodiments to demonstrating an improvement in the liver histology findings associated with NASH or NASH with fibrosis or cirrhosis as determined by the NAS score or percent collagen.

In some embodiments, the method of treating comprises the step of obtaining a composition for parenteral or enteral administration comprising a compound in an acceptable pharmaceutical carrier. In some embodiments, the compound is a polysaccharide and may be chemically defined as galacto-rhamnogalacturonate, a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal). Other side chain minor constituents may include arabinose (Ara), xylose (Xyl), glucose (Glu), and fucose (Fuc).

In some embodiments, the compound is a polysaccharide and may be chemically defined as a subtype of galacto-rhamnogalacturonate termed galactoarabino-rhamnogalacturonate, a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal) and 1,5alpha L arabinose (Ara) residues. Other side chain minor constituents may include xylose (Xyl), glucose (Glu), and fucose (Fuc).

In some embodiments the galacto-rhamnogalacturonate compound can be produced by the method described in U.S. Pat. No. 8,236,780 and in International Patent Application No. PCT/US12/55311 entitled "Composition of Novel Carbohydrate Drug for Treatment of Human Diseases", which are incorporated by reference in their entirety for all purposes.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments the compound can be produced by a process comprising depolymerization catabolized by targeted peroxidation cleavage of glycosidic bonds by ionized OH sup-generated from ascorbic acid and/or peroxide in presence or absence of additional reduced form of a transition metal ion, like Cu sup.++. at 1 to 100 mM. Other transition metals like Ca. sup.++ or Fe.sup.++ can also be used for this purpose.

In some embodiments, the depolymerized compound can be exposed to pH of between 8 to 10, for 10 to 30 minutes at temperature of 2 to 60° C. to initiate controlled limited demethoxylation to generate a depolymerized compound with a degree of methoxylation of 40 to 70 percent in comparison to initial levels of maximum 87% and can be referred to as middle-methoxylated compound. Complete methoxylation of galacturonic acid is considered to be approximately DE 87%.

In some embodiments, the depolymerized composition can be exposed to multiple washes of hot acidic alcohol (e.g at temperatures ranging from 30 to 80° C.) to remove any residual endotoxin, copper and heavy metals, agricultural contaminates and other impurities.

In some embodiments, the compound is a polysaccharide chemically defined as galacto-rhamnogalacturonate or galactoarabino-rhamnogalacturonate, a branched heteropolymer with average molecular weight distribution of 2,000 to 80,000, or 20,000 to 70,000, or 5,000 to 55,000 Daltons, as determined by SEC-RI and/or the SEC-MALLS methods.

In some embodiments, the molar percent of 1,5-α-L-Ara residues in the compound of the present invention may be zero or only found in trace amounts of up to 1%.

In some embodiments, the compound is a galactoarabino-rhamnogalacturonate having a molar percent of the 1,4-β-D-Gal and 1,5-α-L-Ara residues that can exceed 10% of the total molar carbohydrates with approximate ratio ranging from 1:1 to 3:1 respectively.

In some embodiments, the compound can be a highly soluble modified polysaccharide sufficiently reduced in molecular weight range, for example from about 2,000 to about 80,000 D, so as to be compatible with therapeutic formulations for pluralistic administration via routes including but not limited to intravenous, subcutaneous, intra-articular, inhaled, and oral.

In some embodiments, the compound can be synthesized from natural, highly branched, minimally processed and high methoxylated USP pectin which may come from any plant sources, including but not limited to, citrus fruits, apple, or beet.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments the compound can be produced by a process comprising depolymerization catabolized by targeted peroxidation cleavage of glycosidic bonds by ionized OH sup-generated from ascorbic acid and/or peroxide in presence or absence of additional reduced form of a transition metal ion, like Cu sup.++. at 1 to 100 mM. Other transition metals like Ca. sup.++ or Fe.sup.++ can also be used for this purpose.

In some embodiments, the depolymerized compound can be exposed to pH of between 8 to 10 for 10 to 30 minutes at temperature of 2 to 30° C. to initiate controlled limited demethoxylation to generate a depolymerized compound with a degree of methoxylation of 40 to 70 percent in comparison to initial levels of maximum 87% and can be referred to as middle-methoxylated compound. Complete methoxylation of galacturonic acid is considered to be approximately DE 87%.

In some embodiments, the depolymerized composition can be exposed to multiple washes of hot acidic alcohol (50-65° C.) to remove any residual endotoxin, copper and heavy metals, agricultural contaminates and other impurities.

In some embodiments, soluble chemically altered galacto-rhamnogalacturonates are prepared by modifying naturally occurring polymers to reduce the molecular weight for the desired range, reducing the alkylated group (de-methoxylation or deacetylation). Prior to chemical modification, the natural polysaccharides may have a molecular weight range of between about 40,000-1,000,000 D with multiple branches of saccharides, for example, branches comprised of 1 to 20 monosaccharides of glucose, arabinose, galactose etc, and these branches may be connected to the backbone via neutral monosaccharides such as rhamnose. These molecules may further include a single or chain of uronic acid saccharide backbone that may be esterified from as little as about 2% to as much as about 70%. The multiple branches themselves may have multiple branches of saccharides, the multiple branches optionally including neutral saccharides and neutral saccharide derivatives creating mainly hydrophobic entities.

In some embodiments, the galacto-rhamnogalacturonate composition may be produced by various treatments, including heat, high or low pH, various forms of molecular weight exclusion filtration (or combinations of these methods) using raw pectin material from any plant source including but not limited to apple, citrus, or beet pectin, some of which are available commercially as USP pectin material.

In some embodiments, the compound falls within the general class comprising a substantially demethoxylated polygalacturonic acid backbone having rhamnose residues pendent therefrom. It is believed that in materials of this type, the terminal galactose units pendent from the backbone bind to galectin proteins. The remaining bulk of the molecule can potentiate the compound's action in moderating immune system response. While not wishing to be bound by speculation, the remaining bulk of the molecule may either interact with remaining portions of the galectin protein and/or may prolong the binding of the sugar portion thereto.

In some embodiments, the therapeutic compositions may be administered orally, by intravenous injection, by subcutaneous injection or by infusion.

While the foregoing discussion has been primarily directed to therapeutic materials based upon modified pectins, it is to be understood that the present invention is not so limited. In accord with the general principles of the present invention, any member of the broad class of compounds which can interact with and block galectins may be employed. These materials, in an embodiment, comprise carbohydrate materials, since such materials are low in toxicity and exhibit strong interaction with galectins or exhibit a strong anti-inflammatory effect. Modified pectin materials comprise one particularly group of carbohydrate materials. Likewise, synthetic and semi-synthetic analogs thereof such as polygalacturonic acid materials may be similarly employed.

Yet another class of materials of the present invention comprises molecules which have a first portion, which is typically a carbohydrate, and which is capable of binding to galectins, joined to a second portion which inactivates or otherwise moderates the activity of a protein. This second portion need not be a carbohydrate and can comprise a material which cross links or otherwise denatures the segment of protein comprising an active portion of the galectin protein, or an active portion of another protein which interacts with the galectin. Such materials include active species such as sulfur or other chalcogen elements alone or in combination such as thiols, sulfhydryls and the like. Other active species may comprise cyano groups, thiocyanates, alkylating agents, aldehydes and the like. Some active species may be proteins including but not limited to monoclonal antibodies.

Some aspects of the invention relate to a NASH therapeutic formulation having a suitable or increased efficacy in the treatment of NASH or NALD. In some embodiments, the NASH therapeutic formulation includes an effective dose of a galacto-polysaccharide. In some embodiments, the NASH therapeutic formulation can be administered alone or co-administered with an effective dose of a therapeutic agent in a mixture or regimen. The formulation may further include an additional NASH therapeutic agent or excipients in which the formulation is in a powder form or in a liquid form.

In another embodiment, an effective dose of a galactose-containing polysaccharide can be administered in a formulation for oral administration. The formulation may include methods of physical alterations of the compound or additions of various agents that enhance the oral absorption of the galactose-containing polysaccharide.

In some embodiment, the galacto-rhamnogalacturonate can be used in admixture. The term "admixture" means more than one component mixed together to form a combination. For purposes of the present invention, "admixture" means the mixture of two or more compounds at any time prior or subsequent to, or concomitant with, administration.

In some embodiments, the compound is a galacto-rhamnogalacturonate and can be used in combination with a therapeutically effective amount of cysteamine or a pharmaceutically acceptable salt thereof, or cystamine or a pharmaceutically acceptable salt thereof. [see U.S. Pat. No. 7,994,226, incorporated expressly by reference for all purposes.]

In some embodiments, the compound is a galacto-rhamnogalacturonate and can be used in combination with a therapeutically effective amount of various anti-oxidant compounds including but not limited to parenteral or oral administration of compositions comprising glycyrrhizin, schisandra, ascorbic acid, L-glutathione, silymarin, lipoic acid, and d-alpha-tocopherol. [see U.S. Pat. No. 7,078,064, incorporated expressly by reference for all purposes.]

In some embodiments, the compound is a galacto-rhamnogalacturonate and can be used in combination with a therapeutically effective amount of various anti-oxidant compounds including but not limited to parenteral or oral administration of compositions comprising a water soluble Vitamin E preparation, mixed carotenoids, or selenium [see U.S. Pat. No. 6,596,762, incorporated expressly by reference for all purposes.]

In some embodiments, the compound is a galacto-rhamnogalacturonate and can be used in combination with a therapeutically effective amount of parenteral or oral administration of lecithin or vitamin B complex [see U.S. Pat. Nos. 7,018,652; 6,180,139, incorporated expressly by reference for all purposes.]

In some embodiments, the compound is a galacto-rhamnogalacturonate and can be used in combination with a therapeutically effective amount of bile salt preparations including but not limited to ursodeoxycholic acid, chenodeoxycholic acid of other naturally occurring or synthetic bile acids or bile acid salts. [see U.S. Pat. No. 6,297,229, incorporated expressly by reference for all purposes.]

In some embodiments, the compound is a galacto-rhamnogalacturonate and can be used in combination with a therapeutically effective amount of antagonists and/or inverse agonists of the Cannabinoid-1 (CB1) receptor. [see U.S. Pat. Nos. 7,999,107; 7,906,652, incorporated expressly by reference for all purposes.]

In some embodiments, the compound is a galacto-rhamnogalacturonate and can be used in combination with a therapeutically effective amount of a PPAR (peroxisome proliferator-activated receptor) activity regulators. [see U.S. Pat. No. 7,994,353, incorporated expressly by reference for all purposes.]

In some embodiments, the compound is a galacto-rhamnogalacturonate and can be used in combination with a therapeutically effective amount of a benzothiazepine or benzothiepine compound represented by the following formula having a thioamide bond and a quaternary ammonium substituent. [see U.S. Pat. No. 7,973,030, incorporated expressly by reference for all purposes.]

In some embodiments, the compound is a galacto-rhamnogalacturonate and can be used in combination with a therapeutically effective amount of an RNA antisense construct to inhibit protein tyrosine phosphatase PTPRU. [see U.S. Pat. No. 7,897,583, incorporated expressly by reference for all purposes.]

In some embodiments, the compound is a galacto-rhamnogalacturonate and can be used in combination with a therapeutically effective amount of a heteroatom-linked substituted piperidine and derivatives thereof useful as histamine H.sub.3 antagonists. [see U.S. Pat. No. 7,846,946, incorporated expressly by reference for all purposes.]

In some embodiments, the compound is a galacto-rhamnogalacturonate and can be used in combination with a therapeutically effective amount of a axacyclopentane derivative that inhibits stearoyl-coenzyme alpha delta-9 desaturase. [see U.S. Pat. No. 7,754,745, incorporated expressly by reference for all purposes.]

In some embodiments, the compound is a galacto-rhamnogalacturonate and can be used in combination with a therapeutically effective amount of a acylamide compound having secretagogue or inducer activity of adiponectin. [see U.S. Pat. No. 7,732,637, incorporated expressly by reference for all purposes.]

In some embodiments, the compound is a galacto-rhamnogalacturonate and can be used in combination with a therapeutically effective amount of quaternary ammonium compounds. [see U.S. Pat. No. 7,312,208, incorporated expressly by reference for all purposes.]

In some embodiments, the compound is a galacto-rhamnogalacturonate and can be used in combination with a therapeutically effective amount of a isoflavone compound. [see U.S. Pat. No. 6,592,910, incorporated expressly by reference for all purposes.]

In some embodiments, the compound is a galacto-rhamnogalacturonate and can be used in combination with a therapeutically effective amount of a macrolide antibiotic. [see U.S. Pat. No. 5,760,010, incorporated expressly by reference for all purposes.]

In some embodiments, the compound is a galacto-rhamnogalacturonate and can be used in combination with a therapeutically effective amount of Glatiramer acetate (also known as Copolymer 1, Cop-1, or Copaxone—as marketed by Teva Pharmaceuticals), an immunomodulator drug currently used to treat multiple sclerosis.

In some embodiments, the compound is galacto-rhamnogalacturonate and can be used in combination with a therapeutically effective amount of a stain, for example but not limited to HMG-CoA reductase inhibitors such as atorvastatin and simvastatin.

In some embodiments, the compound is a galacto-rhamnogalacturonate and can be used in combination with a therapeutically effective amount of an n-acetyl cysteine, In some embodiments, the compound is a galacto-rhamnogalacturonate and can be used in combination with a therapeutically effective amount of another galectin inhibitor that may inhibit single galectin proteins or a set of galectin proteins including but not limited small organic inhibitors of galectin, monoclonal antibodies, RNA inhibitors, small binding peptides, or protein inhibitors.

In some embodiments, the compound is a galacto-rhamnogalacturonate and can be used in combination with a therapeutically effective amount of a monoclonal antibody to inhibit lysyl oxidase or monoclonal antibody that binds to connective tissue growth factor, In another embodiment, the compound is a galacto-rhamnogalacturonate and can be used in combination with a therapeutically effective amount of pentraxin proteins, including but not limited to recombinant pentraxin-2.

In some embodiments, the galacto-rhamnogalacturonate and other compounds described, are proposed as therapy alone or in combination with other compounds listed above, for human NASH as a method of ameliorating or reversing hepatocyte fat accumulation, intra-portal and intra-lobular inflammatory infiltrate, and fibrosis, including but not limited to collagen deposition in the peri-sinusoidal space, cirrhosis, and for preventing progression to hepatocellular carcinoma. Moreover, it is proposed that these improvements in liver disease pathology will have a resultant positive effect on the health of the individuals by reducing complications of liver fibrosis and cirrhosis, including the development of hepatocellular carcinoma.

In some embodiments, an effective dose of galactose-containing polysaccharide can be administered via a variety of routes including, parenteral via an intravenous infusion given as repeated bolus infusions or constant infusion, intradermal injection, subcutaneously given as repeated bolus injection or constant infusion, or oral administration.

An effective parental dose (given intravenously, intraperitoneally, or subcutaneously) of galactose containing polysaccharide to an experimental animal is within the range of 2 mg/kg up to 160 mg/kg body weight, or 10 mg/kg, or 30 mg/kg, or 60 mg/kg, or 90 mg/kg, or 120 mg/kg body weight.

An effective parenteral dose (given intravenously, intraperitoneally, or subcutaneously) of galactose containing polysaccharide to an experimental animal can be administered three times weekly, twice weekly, once weekly, once every two weeks, once monthly, or as a constant infusion.

An effective parental dose (given intravenously or subcutaneously) of galactose containing polysaccharide to a human subject is within the range of 0.5 mg/kg up to 25 mg/kg body weight, or 1 mg/kg, or 2 mg/kg, or 5 mg/kg, or 7.5 mg/kg, or 10 mg/kg body weight, or 15 mg/kg body weight.

An effective parenteral dose (given intravenously or subcutaneously) of galactose containing polysaccharide to a human subject can be administered three times weekly, twice weekly, once weekly, once every two weeks, once monthly, or as a constant infusion.

In some embodiments, a therapeutically effective dose can be evaluated by a change of at least 10% in the level of the serum biomarkers of NASH, including but not limited to hyaluronic acid and other breakdown products of collagens, cytokeratin-18 and other cytoskeletal cellular proteins, tissue inhibitor of metalloprotease I and II and other liver derived collagen and matrix proteases. These compounds and biomarkers may be measured in serum or liver tissue using immunoassays and the levels correlated with severity of disease and treatment.

In some embodiments, a therapeutically effective dose can be evaluated by a change of at least 10% in serum biomarkers of NASH including but not limited to reactive oxygen products of lipid or protein origin, coenzyme Q reduced or oxidized forms, and lipid molecules or conjugates. These biomarkers can be measured by various means including immunoassays and electrophoresis and their levels correlated with severity of disease and treatment.

In some embodiments, a therapeutically effective dose can be evaluated by a change of at least 10% in serum biomarkers of NASH including but not limited to cytokines that include but are not limited to TNF-alpha, TGF-beta or IL-8, osteopontin, or a metabolic profile of serum components that is indicative of NASH presence or severity (these include serum and urine markers). A profile of one or more of these cytokines, as measured by immunoassay or proteomic assessment by LC mass spec, may provide an assessment of activity of the disease and a marker to follow in therapy of the disease.

In some embodiments, a therapeutically effective dose can be evaluated by a change of at least 10% in the pathophysiologic spectrum of NASH which includes histopathological findings on liver biopsy that include but are not limited to evidence of intra-hepatocellular fat, hepatocellular toxicity including but not limited to hyaline bodies, inflammatory cell infiltrates (including but not limited to lymphocytes and various subsets of lymphocytes and neutrophils), changes in bile duct cells, changes in endothelial cells, number of Kupffer cell macrophages, collagen deposition (including but not limited to peri-sinusoidal, portal and central collagen deposition and portal to central bridging collagen deposition, hepatocellular nodules that distort the normal architecture, hepatocellular atypia consistent with malignant transformation, and various scales and methods that combine various sets of observations for grading the severity of NASH. Such histological assessments are the sine-qua-non of NASH diagnosis and therefore integrally related to assessment of therapy.

In some embodiments, a therapeutically effective dose can be evaluated by a change of at least 10% in the clinical manifestations of NASH including but not limited to clinical testing of stage and severity of the disease, clinical signs and symptoms of disease, and medical complications. Clinical testing of stage and severity of NASH include but are not limited to hematologic testing (including but not limited to red blood cell count and morphology, white blood cell count and differential and morphology, platelet count and morphology), serum or plasma lipids including but not limited to triglycerides, cholesterol, fatty acids, lipoprotein species and lipid peroxidation species, serum or plasma enzymes (including but not limited to aspartate transaminase (AST), alanine transaminase (ALT), alkaline phosphatase (AP), gamma glutamyltranspeptidase (GGTP), lactate dehydrogenase (LDH) and isoforms, serum or plasma albumin and other proteins indicative of liver synthetic capacity, serum or plasma levels of bilirubin or other compounds indicative of the ability of the liver to clear metabolic byproducts, serum or plasma electrolytes (including but not limited to sodium, potassium, chloride, calcium, phosphorous), coagulation profile including but not limited to prothrombin time (PT), partial thromboplastin time (PTT), specific coagulation factor levels, bleeding time and platelet function. Clinical testing also includes but is not limited to non-invasive and invasive testing that assesses the architecture, structural integrity or function of the liver including but not limited to computerized tomography (CT scan), ultrasound (US), ultrasonic elastography (including but not limited to FibroScan) or other measurements of the elasticity of liver tissue, magnetic resonance scanning or spectroscopy, percutaneous or skinny needle or transjugular liver biopsy and histological assessment (including but not limited to staining for different components using affinity dyes or immunohistochemistry), measurement of hepatic portal-venous wedge pressure gradient, or other non-invasive or invasive tests that may be developed for assessing severity of NASH in the liver tissue.

In some embodiments, a therapeutically effective dose can be evaluated by a change of at least 10% in clinical signs and symptoms of disease include fatigue, muscle weight loss, spider angiomata, abdominal pain, abdominal swelling, ascites, gastrointestinal bleeding, other bleeding complications, easy bruising and ecchymoses, peripheral edema, hepatomegaly, nodular firm liver, somnolence, sleep disturbance, and coma. Medical complications of NASH are related to cirrhosis and include ascites, peripheral edema, esophageal and other gastrointestinal tract varices, gastrointestinal bleeding, other bleeding complications, emaciation and muscle wasting, hepatorenal syndrome, and hepatic encephalopathy. An additional complication of NASH related cirrhosis is the development of complications sufficiently severe to warrant placement on liver transplantation list or receiving a liver transplantation.

In some embodiments, a therapeutically effective dose has an effect on NASH liver disease and/or fibrosis in the absence of any effect on whole blood glucose in patients with diabetes or serum lipids in patients with elevated serum lipids.

In some embodiments, a therapeutically effective dose can be evaluated by a reduction of at least 10% in the level of galectin-3 in liver tissue or serum.

In some embodiments, a therapeutically effective dose can be evaluated by a change in the level of galectin-3 in serum.

EXAMPLE 1

Method of Manufacturing Galacto-Rhamnogalacturonate Compound

The following is merely an illustrative example of the production of a therapeutic polysaccharide that is not meant to limit the invention. In this case, the galacto-rhamnogalacturonate produced has been labeled GR-MD-02 in this application.

Apple pectin USP HM (50 kg) was dissolved and heated in water to 35-85° C. 1M HCl or NaOH was added in order to pH-adjust the solution to pH 5-7 and mixed well. The mixing was continued for 2 hours at the 35-85° C. set point. 1M NaOH or HCl was added as needed to readjust pH to between 5 and 7. Solution was cooled to 30° C. At 30° C., pH was adjusted to between 5 and 7.

$CuSO_4$ is added to the pH-adjusted pectin solution so as to result in a final 1 mM $CuSO_4$ concentration. The 1 mM $CuSO_4$ solution was mixed for 30 minutes at a temperature of between 10° C. and 30° C.

At the conclusion of the 30 minute, 1 mM $CuSO_4$ mixing step, 50 grams sodium ascorbate was added (amount was pre-calibrated to achieve the desired MW) and mixed for 5 to 20 minutes. $H_2O_2$ was added start with 0.02 and up to 1.0 moles/kg pectin (pre-calibrated for initial starting pectin MW) and the $H_2O_2$ concentration was maintained for 4 hours (using quantitative test, Sigma, St-Louis) while the solution pH was maintained between 4 and 7.

5M NaOH was added to the solution so as to result in a solution pH of between 8 and 10. The pH-adjusted solution was mixed for 10-30 minutes. Concentrated HCL was then added to the pH-adjusted solution to adjust the pH of the solution to between 4 and 5. The solution, once adjusted to pH between 4 and 5 can be kept mixing for 2 to 24 hours between 2° C. and 8° C.

Solution was then heated to 80° C. for 30-180 minutes and 1-5 kg of Filter-Aid was added (Celite) to the solution, and the solution with added Celite was stirred for 30 minutes and then filtered. The solids resulting from the filtration were discarded.

The filtrate was concentrated 1.5-3× under vacuum, and then pH-adjusted to between 3 and 5. Hot ethanol or isopropanol was added on a 50% weight. The mixture was stirred 1-2 hours to precipitate product, and the mixture was then filtered. The filtrate was discarded, leaving a white to off-white precipitate.

Cold 96% EtOH was added to the solution and the resulting slurry was then stirred for 30 minutes. The solution was filtered and the filtrate was discarded. The 96% EtOH slurry step was repeated, followed by a final filtration and recovery of the white to off-white precipitate.

EXAMPLE 2

Method of Treatment of a Mouse Model of Steatohepatitis

The experimental model used in this example is the mouse in which diabetes was induced and a high fat diet was administered, a model that has been called STAM mice. As shown in FIG. 1, diabetes is induced immediately following birth with a single injection of streptozotocin and then four weeks later the mice are started on a high fat diet. This is a proven model in which the mice consistently develop NASH with hepatocyte fat accumulation, evidence of hepatocyte toxicity, portal and lobular inflammatory infiltrates, peri-sinusoidal fibrosis, advanced fibrosis with nodule formation, cirrhosis, and ultimately hepatocellular carcinoma in a certain percentage of animals.

The progression of disease appearance is fatty liver (FL) by five weeks of age, steatohepatitis (NASH) by 7 weeks of age, fibrosis (Fib) by 9 weeks of age, nodule formation (N) by 13 weeks of age, and some animals developing hepatocellular carcinoma (HC) by 16 weeks of age (FIG. 1).

GR-MD-02, produced as described in Example 1, was given in a dose of 60 mg/kg twice weekly intravenously for four (4) weeks at the each of the starting times indicated. Early treatment was given for weeks 6 through 9 and late therapy was given for weeks 9 through 12.

Figure 2:
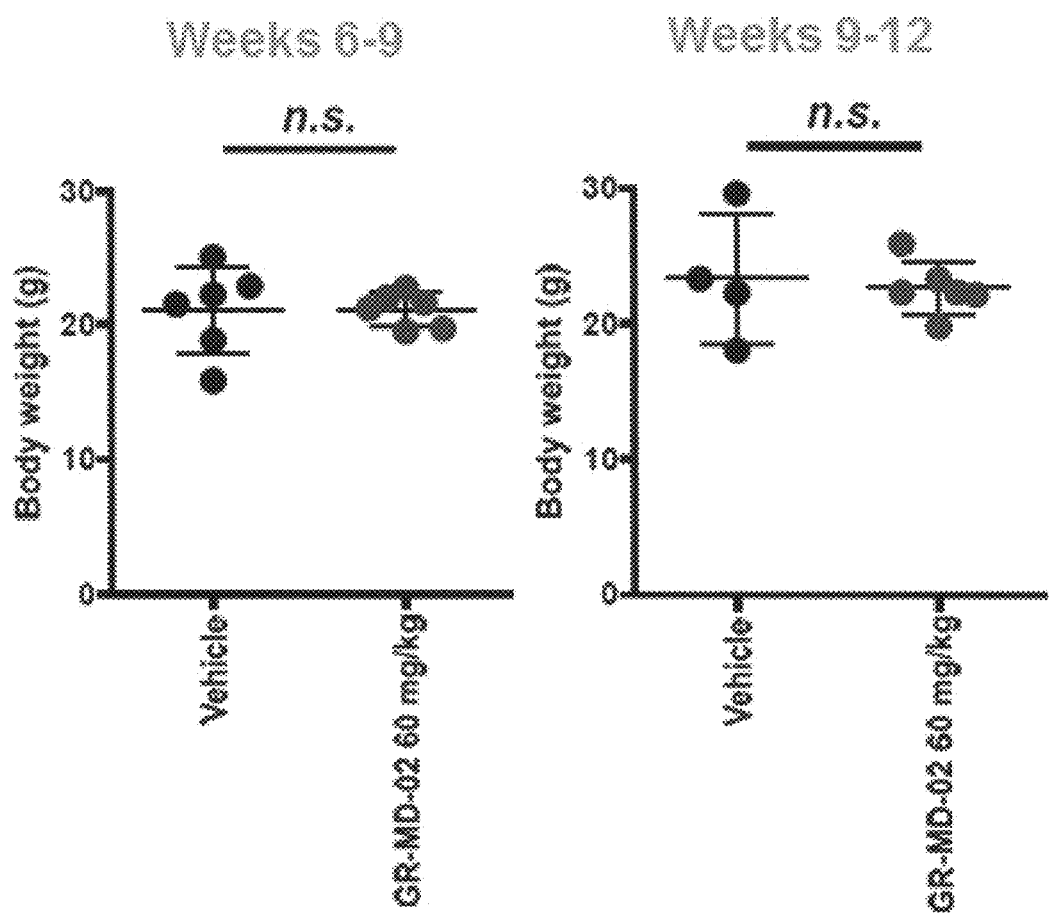
FIG. 2A is a graph showing the changes in body weight of STAM mice in the treatment groups at weeks 6-9.
FIG. 2B is a graph showing the changes in body weight of STAM mice in the treatment groups at weeks 9-12.

The changes in body weight of animals sacrificed after the early and late treatment periods are shown in FIGS. 2A-2B. Three was no difference in body weight for animals treated with vehicle (normal saline alone) as compared to animals treated with GR-MD-02. This indicates at a gross level that there was little or no toxic effect of the treatments on the animals and any changes detected are unlikely due to the overall health of the animals.

Figure 3:
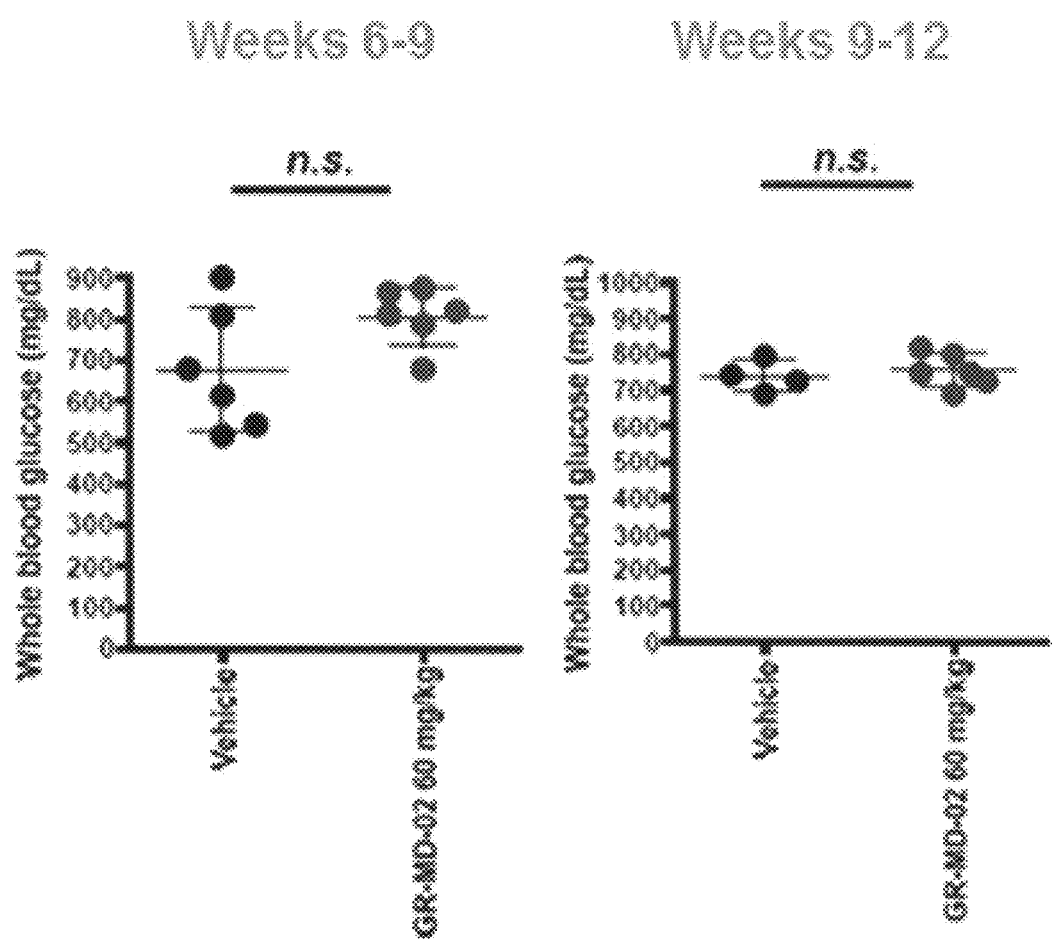
FIG. 3A is a graph showing the comparison of whole blood glucose in STAM mice between the treatment groups at weeks 6-9.
FIG. 3B is a graph showing the comparison of whole blood glucose in STAM mice between the treatment groups at weeks 9-12.

The comparison of whole blood glucose between treatment groups is shown in FIGS. 3A-3B. This shows that the blood glucose levels were markedly elevated in both the vehicle control and GR-MD-02 groups with no statistical differences at either the early or late treatment schedule. The normal blood glucose in mice was approximately 100 mg/dL and the average in the STAM animals was between 700 and 800 mg/dL, hence demonstrating that all animals had overt diabetes.

Figure 4:
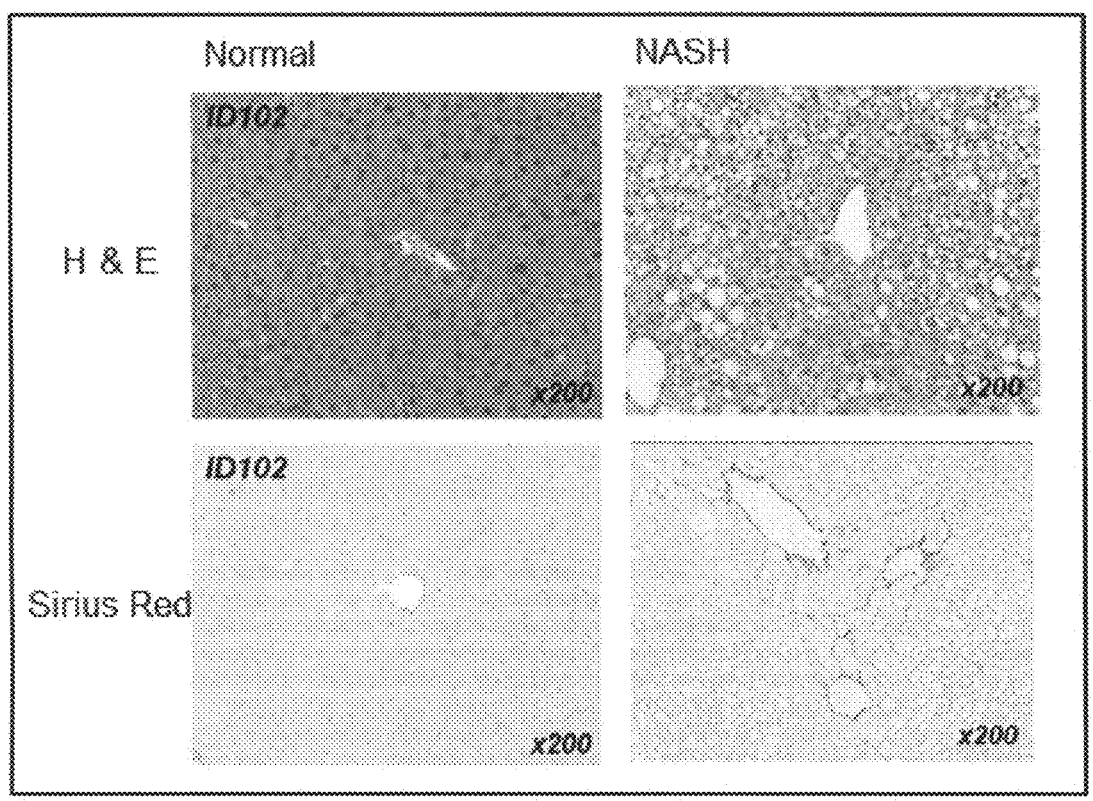
FIG. 4 shows the histology of the normal and NASH mouse model stained with hematoxylin and eosin (H&E) and with Sirius Red.

FIG. 4 shows the histology of the liver in normal and NASH mice. Liver sections stained with hematoxylin and eosin (H&E) show a marked difference between the normal liver and NASH liver, with the NASH liver showing large fat filled hepatocytes, ballooning degeneration of hepatocytes and an infiltrate of inflammatory cells. Liver sections stained with Sirius red highlight the presence of type I collagen. FIG. 4 shows very little collagen in the normal liver, but increased collagen localized around central veins and in the peri-sinusoidal space in the NASH liver. This result demonstrates that the pathology of NASH was achieved in this mouse model.

The NFLD activity score was used to evaluate the severity of liver disease on histological sections of liver and gives points for three aspects of NASH pathology including, steatosis (0 (<5%), 1 (5-33%), 2 (33-66%), or 3 (>66%)), hepatocyte ballooning (0 (none), 1, (few), or 3 (many)), and lobular inflammation (0 (no foci), 1 (<2 foci/200× field), 2 (2-4 foci/200× field), or 3 (>4 foci/200× field)). The total number of points is the NFLD activity score.

Figure 5:
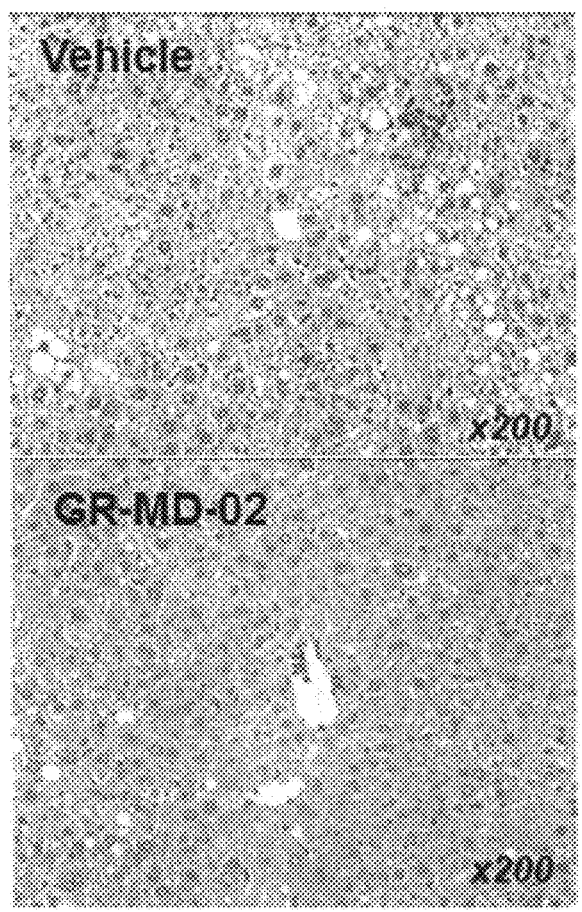
FIG. 5A shows the histology of the vehicle treated and the GR-MD-02 treated NASH mouse model.
FIG. 5B is a graph showing the comparison of the NFLD activity score in STAM mice between the treatment groups.
Figure 5:
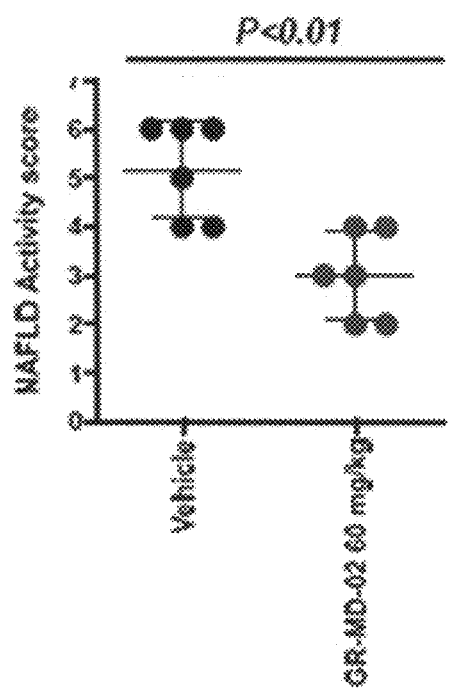

FIG. 5B shows the comparison of NFLD activity score on liver histology in STAM mice between the vehicle and GR-MD-02 treatment groups in the early treatment group. The score for the vehicle treated mice was an average of 5, confirming the presence of NASH. There was a highly statistically significant reduction in the NFLD activity score in the groups of STAM mice treated with GR-MD-02, with an average score of 3 and a p value of less than 0.01 when compared to vehicle animals. These data show that GR-MD-02 reduces the pathology in the liver associated with NASH.

Figure 6:
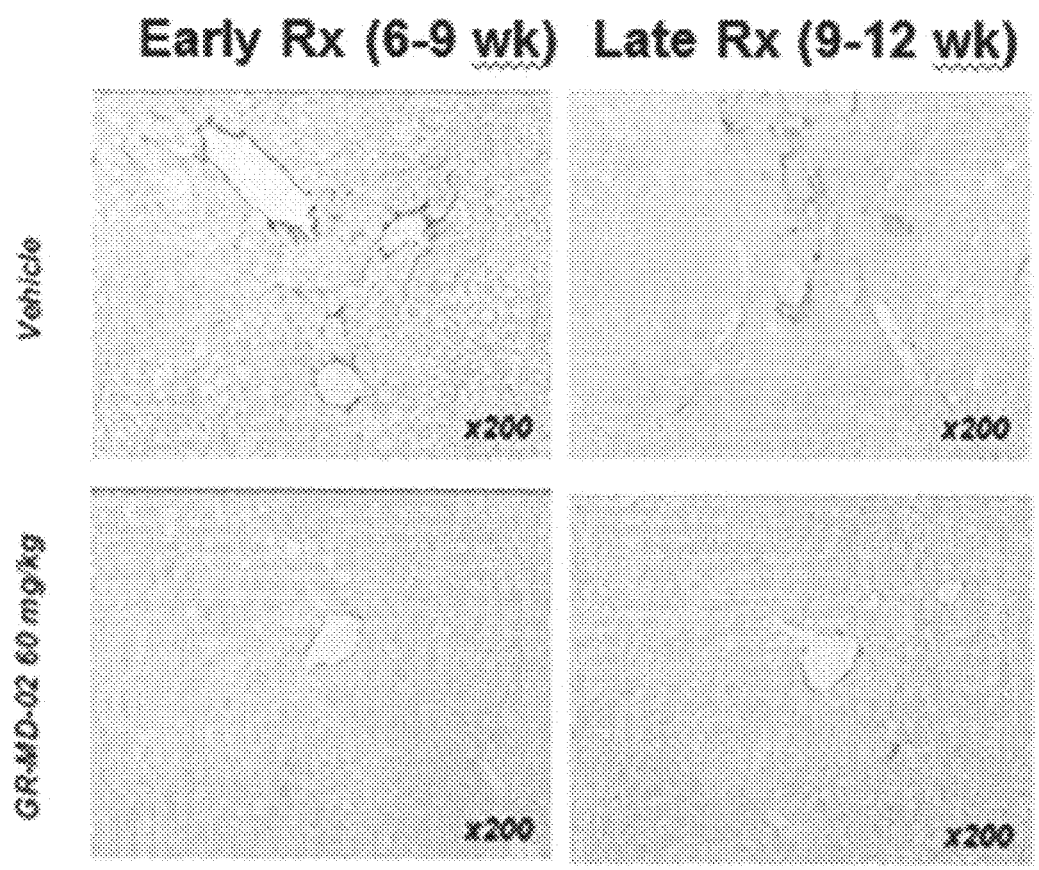
FIG. 6 shows the liver histology with Sirius red staining of experimental groups at 6-9 weeks and at 9-12 weeks.

FIG. 6 shows the comparison of Sirius red-positive area in liver biopsies of STAM mice between the vehicle and GR-MD-02 treatment groups at 6-9 weeks and 9-12 weeks. Sirius red is a histological stain that has a specific affinity for collagen fibers, staining them red, and is therefore a quantitative tool for assessing the degree of fibrosis in liver biopsies. In both the early and late treatment groups there is a marked reduction in Sirius red staining seen in the GR-MD-02 treated animals versus vehicle control.

Figure 7:
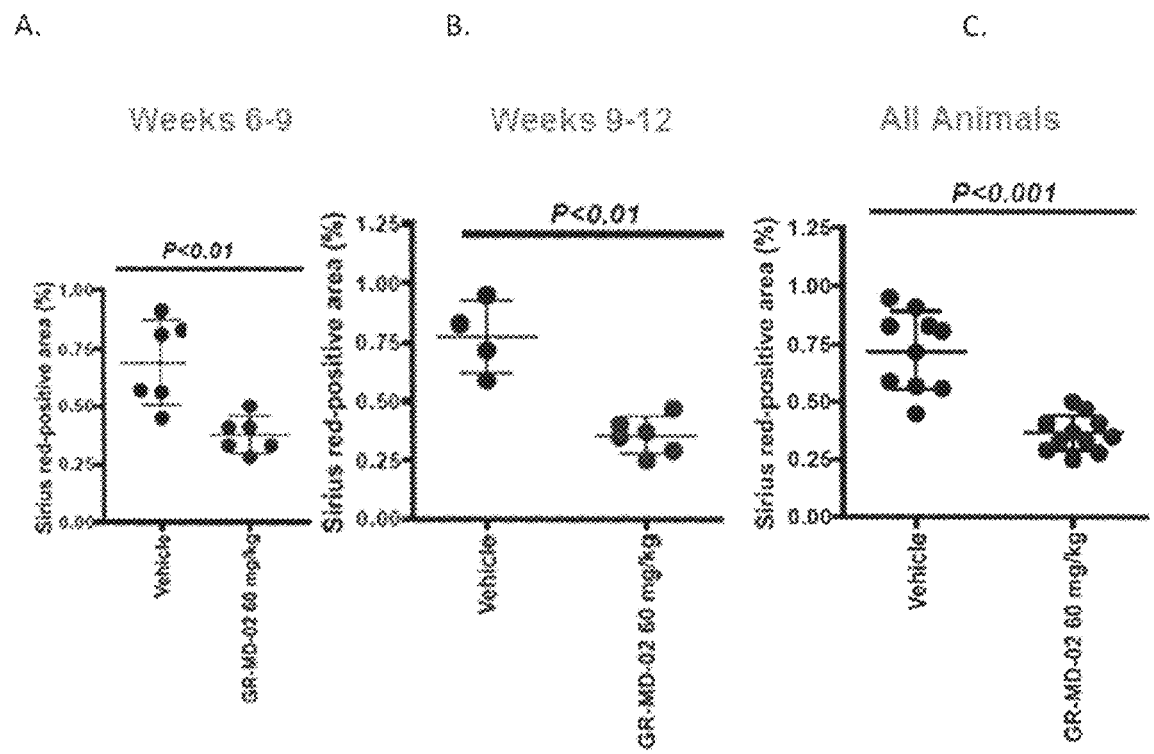
FIG. 7A is a graph showing the comparison of Sirius red-positive area in liver histology between experimental groups at 6-9 weeks.
FIG. 7B is a graph showing the comparison of Sirius red-positive area in liver histology between experimental groups at 9-12 weeks.
FIG. 7C is a graph showing the comparison of Sirius red-positive area in liver histology between experimental groups in all animals.

The area of Sirius red staining on liver histopathological sections from each of the three treatment groups was assessed using computer assisted morphometric analysis. FIGS. 7A, 7B and 7C shows that collagen percent area was markedly statistically significantly reduced in the early and late treatment groups and when assessed combining both groups. These results demonstrate that treatment with GR-MD-02 reduces liver fibrosis in mice with NASH as a result of reducing the activity of NASH. Moreover, the late treatment group shows that treatment with GR-MD-02 is able to reverse fibrosis in the NASH mice (FIG. 7B).

The data further show that the efficacy of the therapeutic compounds tested have an effect on NASH liver disease and fibrosis in the absence of any effect on whole blood glucose. The blood glucose was not reduced in the treatment groups versus the control groups indicating that the liver disease can be treated without effective treatment of diabetes.

Figure 8:
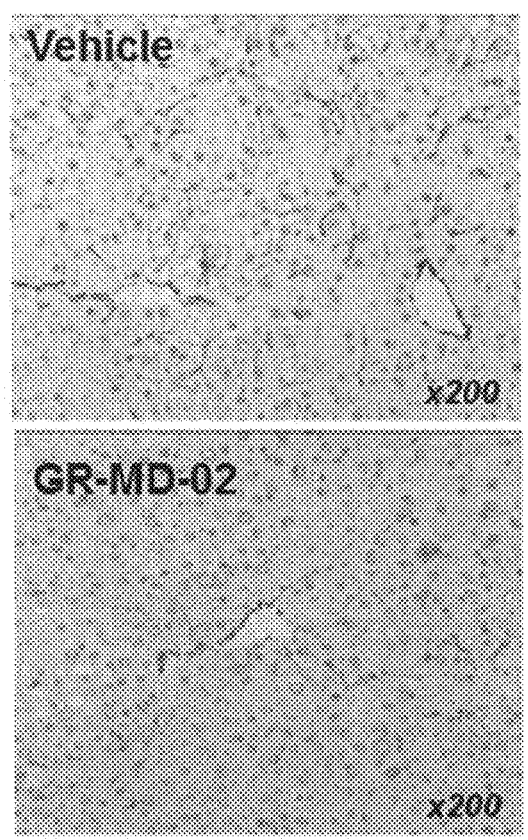
FIG. 8A shows immunohistochemical staining of alpha-Smooth Muscle Actin (SMA) in liver tissue of experimental groups.
FIG. 8B shows digital morphometry of alpha-Smooth Muscle Actin (SMA) in liver tissue of experimental groups.
Figure 8:
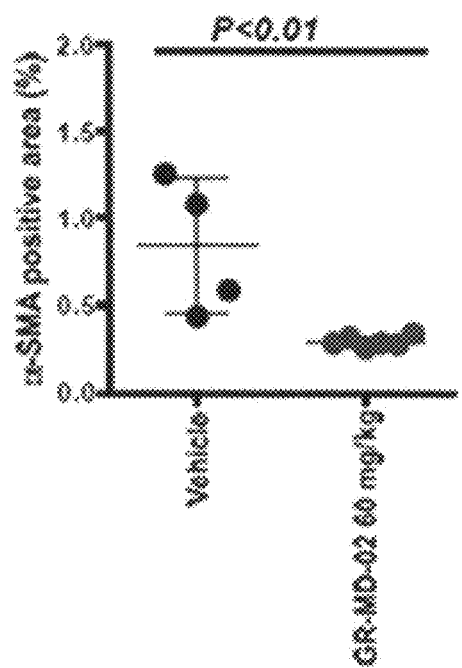

The primary cell that lays down collagen in the liver is the activated stellate cell. The inflammatory infiltrate in NASH activates quiescent stellate cells which, in their activated state, secrete collagen that forms the fibrous tissue associated with the disease. FIG. 8A shows immunohistochemical staining for the protein alpha-Smooth Muscle Actin, which is a marker for activated stellate cells. Treatment with GR-MD-02 caused a marked reduction in alpha-Smooth Muscle Actin which indicates that activated stellate cells are markedly reduced (FIG. 8B). This is one of mechanism for the reduced collagen deposition with treatment.

Figure 9:
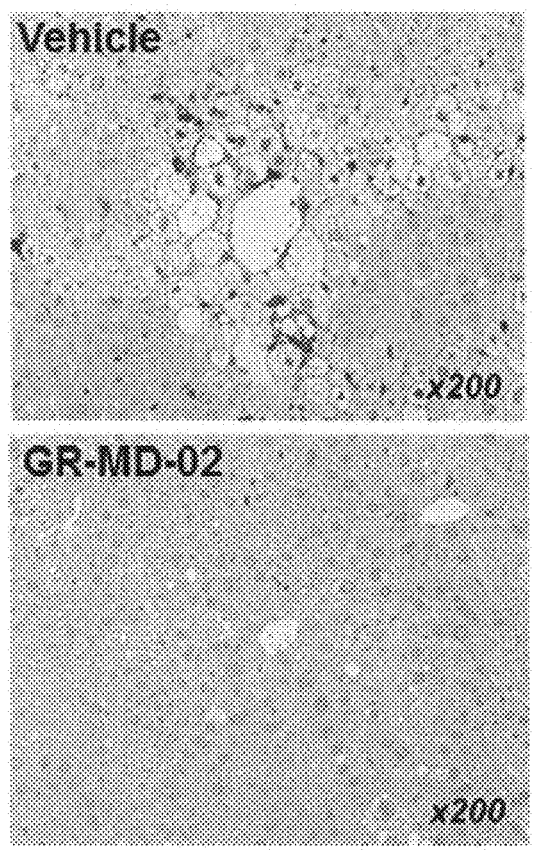
FIG. 9A shows immunohistochemical staining of galectin-3 in liver tissue of experimental groups.
FIG. 9B shows digital morphometry of galectin-3 in liver tissue of experimental groups.
Figure 9:
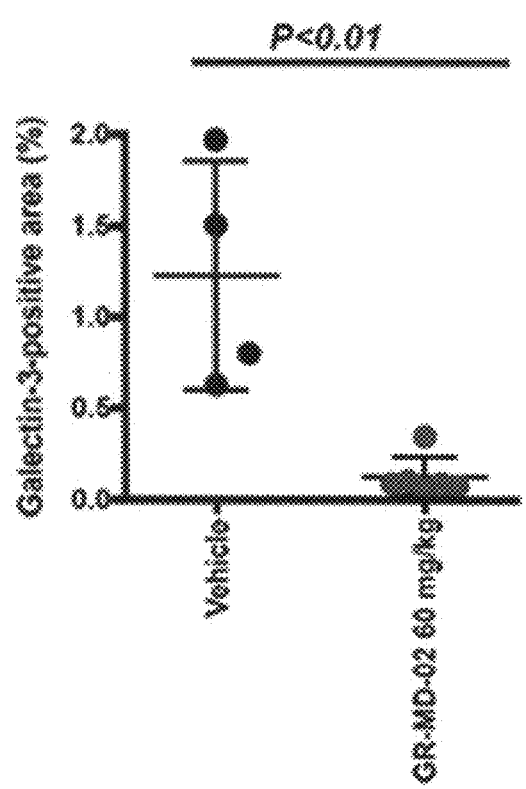

FIG. 9A shows immunohistochemical staining of galectin-3 protein in liver tissue of vehicle and GR-MD-02 treated experimental groups. There was high level expression of galectin-3 predominantly in macrophages in the vehicle treated animal. Treatment with GR-MD-02 resulted in a marked reduction of galectin-3 in the liver associated with improved pathology of the disease (FIG. 9B).

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

The invention claimed is:

1. A method comprising the steps of:
obtaining a composition for parenteral or enteral administration comprising a galacto-rhamnogalacturonate in an acceptable pharmaceutical carrier, wherein the galacto-rhamnogalacturonate comprises a 1,4-linked galacturonic acid (GalA) and methyl galacturonate (MeGalA) residues backbone linked to branched heteropolymers of alternating oligomers of α-1,2 linked rhamnose and α-1, 4-linked GalA residues, the rhamnose residues carrying a primary branching of oligomers of 1,4-β-D-galactose residues,
administering to a subject in need thereof an effective dose of the composition that results in at least one of the following:
reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis, wherein the subject has at least one of the following: fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma.

2. The method of claim 1 wherein the galacto-rhamnogalacturonate further comprises xylose, glucose, fucose residues or combination thereof.

3. The method of claim 1 wherein the galacto-rhamnogalacturonate has an average molecular weight ranging from 5 kDa to 55 kDa.

4. The method of claim 1 wherein the galacto-rhamnogalacturonate has an average molecular weight ranging from 2 kDa to 80 kDa.

5. The method of claim 1 wherein the galacto-rhamnogalacturonate has an average molecular weight ranging from 20 kDa to 70 kDa.

6. The method of claim 1 wherein in the step of administering the galacto-rhamnogalacturonate is co-administered with effective amount of a therapeutic agent.

7. The method of claim 6 wherein the therapeutic agent is one of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activating receptor, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of the foregoing.

8. The method of claim 7 wherein the anti-oxidant compound comprises a water soluble Vitamin E preparation, mixed carotenoids, selenium or combinations thereof.

9. The method of claim 7 wherein the bile salt preparation comprises ursodeoxycholic acid, chenodeoxycholic acid or naturally occurring bile acids or bile acid salts, or synthetic bile acids or bile acid salts or combinations thereof.

10. The method of claim 7 wherein the prentaxin protein is a recombinant pentraxin-2.

11. The method of claim 7 wherein the HMG-CoA reductase inhibitors comprises atorvastatin, simvastatin or combinations thereof.

12. The method of claim 7 wherein the galectin inhibitor comprises small organic inhibitors of galectin, monoclonal antibodies, RNA inhibitors, small binding peptides, protein inhibitors or combinations thereof.

13. The method of claim 7 wherein the antibody is an antibody against lysyl oxidase like-2 enzyme (LOXL2) or an antibody against connective tissue growth factor (CTGF).

14. An admixture having a galacto-rhamnoalacturonate and a therapeutic agent For the treatment of fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma, wherein the galacto-rhamnogalacturonate is a galactoarabino-rhamnogalacturonate, comprising a 1,4-linked galacturonic acid (GalA) and methyl galacturonate (MeGalA) r0esidues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof, and wherein the 1,4-β-D-galactose residues, the 1,5-α-L-arabinose residues or combination thereof represents at least 10 molar percent of the total molar carbohydrates.

15. The admixture of claim 14 wherein the galacto-rhamnogalacturonate has an average molecular weight ranging from 5 kDa to 55 kDa.

16. The admixture of claim 14 wherein the galacto-rhamnogalacturonate has an average molecular weight ranging from 2 kDa to 80 kDa.

17. The admixture of claim 14 wherein the galacto-rhamnogalacturonate has an average molecular weight ranging from 20 kDa to 70 kDa.

18. The admixture of claim 14 wherein the therapeutic agent is one of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of the foregoing.

19. The admixture of claim 14 wherein the 1,4-β-D-galactose and 1,5-α-L-arabinose residues are present in a 2:1 or a 3:1 ratio.

20. The method of claim 1 wherein administration results in reduction of the accumulation of fat in the liver by at least 10%, reduction of the accumulation of fat in the liver as assessed in percentage of hepatocytes with fat in the liver, reduction of the hepatocyte ballooning by at least 10%, reduction of infiltration of neutrophils and lymphocytes by at least 10% in portal, central and lobular areas of a liver specimen, reduction of accumulation of collagen in the liver by at least 5%, or reduction by at least 10% of galectin-3 in liver tissue or serum.

21. The method of claim 20 wherein the reduction in the accumulation of fat in the liver is assessed by ultrasound or magnetic resonance imaging protocols.

22. The method of claim 20 wherein the reduction of hepatocyte ballooning is assessed in percentage of swollen hepatocytes.

23. The method of claim 20 wherein the reduction of the accumulation of collagen in the liver is determined non-invasively by tissue stiffness/elasticity measurement using ultrasound or magnetic resonance elastography.

24. The method of claim 1 wherein the serum markers of nonalcoholic; stent hepatitis activity are selected from the group consisting of transaminases, coenzyme Q reduced or oxidized, or a combination thereof.

25. The method of claim 1 wherein the reduction of the medical consequences of NASH with liver fibrosis or cirrhosis comprises reduction of portal hypertension, reduction in hepatic protein synthetic capability, hyperbilirubinemia, or encephalopathy.

26. A method comprising the steps of:
obtaining a composition for parenteral or enteral administration comprising a galacto-rhamnogalacturonate in an acceptable pharmaceutical carrier, wherein the galacto-rhamnogalacturonate is a galactoarabino-rhamnogalacturonate, comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof;
administering to a subject in need thereof an effective dose of the composition that results in at least one of the following:
reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of non a cohol ic steatohepatitis,
wherein the subject has at least one of the following: fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma.

27. The method of claim 26 wherein administration results in reduction of the accumulation of fat in the liver by at least 10%, reduction of the accumulation of fat in the liver as assessed in percentage of hepatocytes with fat in the liver, reduction of the hepatocyte ballooning by at least 10%, reduction of infiltration of neutrophils and lymphocytes by at least 10% in portal, central and lobular areas of a liver specimen, reduction of accumulation of collagen in the liver by at least 5%, or reduction by at least 10% of galectin-3 in liver tissue or serum.

28. The method of claim 27 wherein the reduction in the accumulation of fat in the liver is assessed by ultrasound or magnetic resonance imaging protocols.

29. The method of claim 27 wherein the reduction of hepatocyte ballooning is assessed in percentage of swollen hepatocytes.

30. The method of claim 27 wherein the reduction of the accumulation of collagen in the liver is determined non-invasively by tissue stiffness/elasticity measurement using ultrasound or magnetic resonance elastography.

31. The method of claim 26 wherein the serum markers of nonalcoholic; steatohepatitis activity are selected from the group consisting of transaminases, coenzyme Q reduced or oxidized, or a combination thereof.

32. The method of claim 26 wherein the reduction of the medical consequences of NASH with liver fibrosis or cirrhosis comprises reduction of portal hypertension, reduction in hepatic protein synthetic capability, hyperbilirubinemia, or encephalopathy.

33. The method of claim 26 wherein the galacto-rhamnogalacturonate further comprises xylose, glucose, fucose residues or combination thereof.

34. The method of claim 26 wherein the galacto-rhamnogalacturonate has an average molecular weight ranging from 2 kDa to 80 kDa, 5 kDa to 55 kDa, or 20 kDa to 70 kDa.

35. The method of claim 26 wherein the 1,4-β-D-galactose and 1,5-α-L-arabinose residues are present in a 2:1 or a 3:1 ratio.

36. The method of claim 26 wherein the 1,4-β-D-galactose residues, the 1,5-α-L-arabinose residues or combination thereof represent at least 10 molar percent of the total molar carbohydrates.

37. The method of claim 26 wherein in the step of administering the galacto-rhamnogalacturonate is co-administered with effective amount of a therapeutic agent.

38. The method of claim 29 wherein the therapeutic agent is one of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of the foregoing.

39. The method of claim 38 wherein the anti-oxidant compound comprises a water soluble Vitamin E preparation, mixed carotenoids, selenium or combinations thereof.

40. The method of claim 38 wherein the bile salt preparation comprises ursodeoxycholic acid, chenodeoxycholic acid of naturally occurring bile acids or bile acid salts, chenodeoxycholic acid of synthetic bile acids or bile acid salts or combinations thereof.

41. The method of claim 38 wherein the prentaxin protein is a recombinant pentraxin-2.

42. The method of claim 38 wherein the HMG-CoA reductase inhibitors comprises atorvastatin, simvastatin or combinations thereof.

43. The method of claim 38 wherein the galectin inhibitor comprises small organic inhibitors of galectin, monoclonal antibodies, RNA inhibitors, small binding peptides, protein inhibitors or combinations thereof.

44. The method of claim 38 wherein the antibody is an antibody against lysyl oxidase or an antibody against connective tissue growth factor.

* * * * *